United States Patent [19]

Yamaguchi et al.

[11] Patent Number: 4,590,215

[45] Date of Patent: May 20, 1986

[54] GROWTH INHIBITOR FOR CARIOGENIC BACTERIA

[75] Inventors: Yuzo Yamaguchi; Toshiya Sato, both of Kanagawa, Japan

[73] Assignee: Takasago Perfumery Co., Ltd., Tokyo, Japan

[21] Appl. No.: 622,598

[22] Filed: Jun. 20, 1984

[30] Foreign Application Priority Data

Jun. 21, 1983 [JP] Japan .................................. 58-110113

[51] Int. Cl.$^4$ ........................................... A61K 31/045
[52] U.S. Cl. .................................... 514/729; 514/835
[58] Field of Search ................................ 514/729, 835

[56] References Cited

PUBLICATIONS

Chem. Abst. 92:175065(b) (1980)–Makarenko et al.
Chem. Abst. 95:103131(j) (1981)–Ji et al.
Chem. Abst. 98:138892(x) (1983)–Makarenko et al.
Chem. Abst. 100:206512k (1984)–Yatagai et al.
Chem. Abst. 102:119450m (1985)–Yamaguchi et al.

Primary Examiner—Douglas W. Robinson
Attorney, Agent, or Firm—Sughrue, Mion, Zinn, Macpeak, and Seas

[57] ABSTRACT

A growth inhibitor for cariogenic bacteria which comprises containing therein l-α-cadinol as an active ingredient. In particular, the effect of growth inhibition to *Streptococcus mutans* IPCR 1009 strain can be produced at a concentration of 1/50,000.

9 Claims, No Drawings

GROWTH INHIBITOR FOR CARIOGENIC BACTERIA

FIELD OF THE INVENTION

The present invention relates to a growth inhibitor for cariogenic bacteria. More particularly, it relates to a growth inhibitor for cariogenic bacteria which comprises containing therein l-α-cadinol as an active ingredient.

BACKGROUND OF THE INVENTION

The caries is generally referred to as a decayed tooth. It is caused by *Streptococcus mutans* and other lactic acid bacteria indigenous to the oral cavity which form lactic acid in the bacterial plaque resulting from sucrose etc. in the food. The lactic acid dissolves calcium in the tooth. (This is called decalcification.)

Heretofore, several attempts have been made to prevent caries. They include use of antibiotics, fungicides, an enzyme which dissolves cell walls and medicines having the antibacterial action to prevent the growth of cariogenic bacteria. They also include use of polysaccharide hydrolase to prevent the formation of bacterial plaque. However, those have a disadvantage of disturbing the bacterial flora in the oral cavity and intestine and destroying the natural balance among bacteria. In addition, the use of antibiotics tend to produce side effects. These disadvantages in practical use have not been overcome yet.

In view of these circumstances, as a result of a series of investigations in search for a material having a high antibacterial activity specifically for cariogenic bacteria, it has been found that some of natural vegetable essential oils have such antibacterial activity, such a material is commonly contained in the essential oils, such is l-α-cadionol, and this material has the properties to achieve the object of this invention. The present invention has been attained on the basis of this finding.

SUMMARY OF THE INVENTION

Accordingly, an object of this invention is to provide a growth inhibitor for cariogenic bacteria which comprises containing therein l-α-cadinol as an active ingredient.

DETAILED DESCRIPTION OF THE INVENTION

The l-α-cadinol used in this invention is the conventional compound represented by the structural formula:

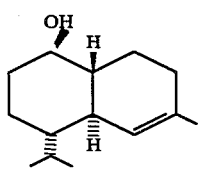

This compound is a colorless crystal having a melting point of 74° to 74.5° C. and an optical rotation of $[\alpha]_D^{20} = -46°$ (in ethanol). The compound is contained in cubeb oil, Java citronella oil, juniper berry oil, and cade oil. The compound is also contained in the creeping pine leave oil produced in Japan.

l-α-Cadinol can be isolated from these essential oils by the conventional method such as fractional distillation or silica gel column chromatography.

The cariogenic bacteria growth inhibitor containing l-α-cadinol according to this invention can be used in the form of a solution by dissolving it in an organic solvent such as ethanol, propylene glycol or glycerine, which casues no problem in the oral cavity, because l-α-cadinol is hardly soluble in water but soluble in an organic solvent such as alcohols. The inhibitor can also be used in the form of an emulsion by emulsifying it in water using a surfactant such as Span 20 (a product of Atlas Powder Co.). Moreover, it is also possible to make such an emulsion into a waterdispersible powder by adding dextrin thereto followed by spray drying. Thus, the growth inhibitor of this invention can be used in various forms depending upon the purpose of use thereof. The inhibitor can, of course, be used in combination with other medicines, if desired.

l-α-Cadinol performs bacteriostatic action on cariogenic bacteria, and its bactericidal action is mild. Therefore, l-α-cadinol can be suitably added to chewing gum, candy, troche, wheat gluten, and other foods which stay in the oral cavity for a long time, in the form of a propylene glycol or glycerine solution. Further, l-α-cadinol can be suitably added to toothpaste and mouth wash in the form of an emulsion and to tooth powder in the form of a powder.

The growth inhibitor of this invention can completely inhibit the growth of *Streptococcus mutans* RIMD 3125001 strain which causes caries under the anaerobic condition in the medium, at a concentration of 1/50,000 of l-α-cadinol. However, when used at the same concentration, the inhibitor did not inhibit at all the growth of enteric bacteria such as *Bacteroides microfusus* IPCR 1009 strain and *Escherichia coli* ATCC 10789 strain (which are both aerobic) and *Bifidobacterium adolescentis* (which is absolutely anaerobic). The inhibitor exhibited a slight antibacterial action against gram-positive bacteria such as *Bacillus subtilis*, *Pseudomonas aeruginosa*, and *Staphylococuss aureus* under the aerobic conditions; but did not exhibit any antibacterial action against gram-negative bacteria and molds such as *Aspergillus nigar*, *Candida albicans*, and *Klebsiella pneumoniae*.

The effectiveness of the growth inhibitor of this invention was not affected by a surfactant such as sodium laurylsulfonate or "Span 20".

Where the cariogenic bacteria growth inhibitor of this invention is incorporated into foods or dentifrice, it is preferred that the concentration thereof be slightly higher than the effective concentration (1/50,000), because the contact time of the food or dentifrice to cariogenic bacteria is comparatively short.

Any essential oil containing l-α-cadinol may be used for the object of this invention. It is however preferred that the essential oil be purified completely or to a certain extent so as not to give off an unpleasant odor in the oral cavity due to other components.

The cariogenic bacteria growth inhibitor of this invention is specifically effective to *Streptococcus mutans* and its effect of inhibiting the growth of bacteria is not affected by a surfactant. l-α-Cadinol is highly safe because it is a component contained in the natural vegetable essential oil. In addition, it tastes only a little and gives no unpleasant feeling when put in the mouth.

This invention is now described by reference to the following examples but is not limited thereto. Unless otherwise indicated, all percents, parts, ratios and the like are by weight.

EXAMPLE 1

2.0 g of l-α-cadinol was dissolved in 98 g of official ethyl alcohol with stirring at room temperature to give 100 g of a solution.

This solution was added to the heart infusion agar medium. *Streptococcus mutans* RIMD 3125001 (designated as A in Table) was transplanted by stabbing to this medium. Incubation was performed at 37° C. for 72 hours. No growth was observed in the medium containing the solution at a concentration of 1/1,000 (or 1/50,000 calculated as l-α-cadinol). Growth was barely observed in the medium containing the solution at a concentration of 1/1,600 (or 1/80,000 calculated as l-α-cadinol).

Then, *Bacteroides microfusus* IPCR 1009 (designated as B in Table 1) and *Escherichia coli* ATCC 10789 (designated as C in Table 1) were transplanted to the above-mentioned medium. Incubation was performed under the aerobic condition at 37° C. for 72 hours. Their growth was inhibited at a concentration of 1/2,000 as l-α-cadinol.

*Bifidobacterium adolescentis* ATCC 15705 (designated as D in Table 1) was transplanted to the same medium as mentioned above, and incubation was performed under the anaerobic condition at 37° C. for 72 hours. The growth was inhibited at a concentration of 1/7,500 as l-α-cadinol.

The same test as above was performed under the aerobic condition for *Pseudomonas aeruginosa* (E), *Bacillus subtilis* (F), *Staphylococuss aureus* (G), *Apergillus nigar* (H), *Candida alibicans* (I), and *Klebiella pneumoniae* (J). The results obtained are shown in Table 1 below.

TABLE 1

| Designation of bacteria | Concentration for growth inhibition (as l-α-cadinol) |
|---|---|
| A | 1/50,000 |
| B | 1/2,000 |
| C | 1/2,000 |
| D | 1/7,500 |
| E | 1/500 |
| F | 1/5,000 |
| G | 1/5,000 |
| H | 1/1,000 |
| I | 1/2,000 |
| J | 1/1,000 |

EXAMPLE 2

2.0 g of l-α-cadinol was dissolved in 6 ml of official ethyl alcohol, and glycerine was then added thereto to give 100 g of a solution.

This solution was added to two kinds of heart infusion agar media, one containing 1.0 g of sodium laurylsulfonate and the other, 1.0% of "Span 20". *Streptococcus mutans* RIMD 3125001 was transplanted to the media. Incubation was performed at 37° C. for 72 hours. The concentration for growth inhibition was 1/1,000 (or 1/50,000 calculated as l-α-cadinol) in both cases. This indicates that the effectiveness of the growth inhibitor is not affected by the surfactant used.

EXAMPLE 3

Creeping pine leave oil was purified by column chromatography so that the concentration of l-α-cadinol was increased to 75%. 10 g of this purified essential oil was mixed with 1 g of "Span 20" and 1 g of "Span 40". To the resulting mixture was added 150 ml of water and 50 g of dextrin, followed by homogenization. The mixture was spray-dried to give 53 g of a powder containing 14.2% of l-α-cadinol.

The antibacterial action of this powder on *Streptococcus mutans* RIMD 3125001 was investigated using the heart infusion agar medium. The concentration for growth inhibition was 1/7,000 as powder, which is equivalent to 1/50,000 as l-α-cadinol.

While the invention has been described in detail and with reference to specific embodiments thereof, it will be apparent to one skilled in the art that various changes and modifications can be made therein without departing from the spirit and scope thereof.

What is claimed is:

1. A composition for inhibiting growth of *Streptococcus mutans*, comprising an antibacterially effective amount of l-α-cadinol and a pharmaceutically acceptable carrier.

2. A composition as claimed in claim 1, wherein l-α-cadinol is present in a concentration of at least 1/50,000 parts by weight.

3. A composition as claimed in claim 1, wherein said pharmaceutically acceptable carrier is an organic solvent.

4. A composition is claimed in claim 3, wherein said organic solvent is selected from the group consisting of ethanol, propylene glycol and glycerine.

5. A composition as claimed in claim 1, wherein emulsification of l-α-cadinol is accomplished with a surfactant.

6. A composition as claimed in claim 1, wherein said pharmaceutically acceptable carrier is chewing gum, candy, troche and wheat gluten 7. A composition as claimed in claim 1, wherein said pharmaceutically active carrier is toothpaste or mouthwash.

8. A composition as claimed in claim 1, wherein said pharmaceutically active carrier is tooth powder.

9. A composition as claimed in claim 1, containing l-α-cadinol in an amount sufficient to inhibit growth of *Streptococcus mutans* RIMD 3125001.

* * * * *